United States Patent [19]

Otten, deceased et al.

[11] 4,361,698
[45] Nov. 30, 1982

[54] PROCESS FOR THE MANUFACTURE OF DIHALOGENOTRIAZINYLAMINO-NAPHTHOL COMPOUNDS

[75] Inventors: Joachim W. Otten, deceased, late of Offenbach am Main, Fed. Rep. of Germany; by Ursula Otten, heir, Heidelberg, Fed. Rep. of Germany; by Anna G. Rudolph née Otten, heir, Dillenburg, Fed. Rep. of Germany; by Fritz Meininger, Frankfurt am Main, Fed. Rep. of Germany

[73] Assignee: Hoechst Aktiengesellschaft, Frankfurt am Main, Fed. Rep. of Germany

[21] Appl. No.: 244,612

[22] Filed: Mar. 17, 1981

[30] Foreign Application Priority Data

Mar. 19, 1980 [DE] Fed. Rep. of Germany ....... 3010502

[51] Int. Cl.³ ......................................... C07D 251/44
[52] U.S. Cl. ................................................... 544/211
[58] Field of Search ........................................ 544/211

[56] References Cited

U.S. PATENT DOCUMENTS

| | | | |
|---|---|---|---|
| 1,551,095 | 8/1925 | Fritzsche et al. | 544/211 |
| 2,728,761 | 12/1955 | Wallace et al. | 544/211 |
| 3,773,827 | 11/1973 | Schundehutte | 544/211 |

*Primary Examiner*—John M. Ford
*Attorney, Agent, or Firm*—Curtis, Morris & Safford

[57] ABSTRACT

Dihalogenotriazinylamino-naphthol compounds of th formula (1)

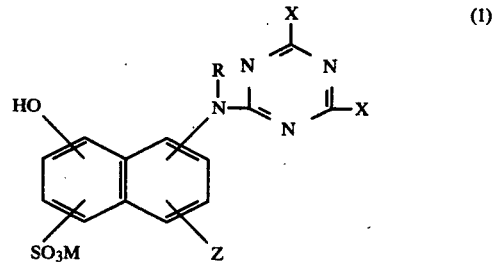

in which the radicals X each mean fluorine, chlorine or bromine, R is hydrogen or alkyl of 1 to 4 C-atoms, M is hydrogen or the equivalent of a metal, and Z is hydrogen or a group of the formula —$SO_3M$ with M having the abovementioned meaning, are prepared in water as reaction medium by reaction of an aminonaphthol compound of the formula (2)

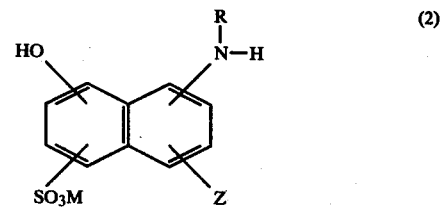

in which R, M and Z have the abovementioned meanings with a cyanuric halide compound of the formula (3)

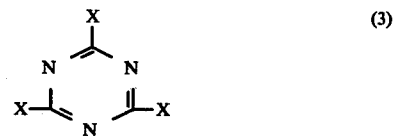

in which the radicals X have the abovementioned meanings, at pH 5 or smaller than 5 by introducing the aminonaphthol compound of the formula (2) in solid, undissolved form into the reaction, and carrying out the reaction in suspension.

4 Claims, No Drawings

PROCESS FOR THE MANUFACTURE OF DIHALOGENOTRIAZINYLAMINO-NAPHTHOL COMPOUNDS

The present invention relates to the manufacture of intermediates which are especially used for further processing to fiber-reactive compounds, such as dyestuffs.

Dihalogenotriazinylamino-naphthol compounds are known. They are prepared by acylation of aminonaphthol compounds with cyanuric halides. According to British Patent Specification No. 221,843, for example, cyanuric chloride is first dissolved in acetone, and subsequently this solution is stirred into ice-water to obtain a finely divided suspension of cyanuric chloride in water. To this suspension, the aminonaphthol-sulfonic acid as the second reactant is subsequently added in the form of an alkaline or neutral aqueous solution.

This operation method which is generally used is also described in more recent literature, for example in W. F. Beech, Fibre-Reactive Dyes (London, 1970), page 152, or in K. Venkataraman, The Chemistry of Synthetic Dyes, Vol. VI-Reactive Dyes (New York and London, 1972), page 262. The aminonaphthol-sulfonic acids used as reaction components are in any case introduced into the acylation reaction in the form of an aqueous, neutral or weakly alkaline solution.

In analogous acylation reactions in which as cyanuric halide there are used cyanuric bromide or cyanuric fluoride as reactants, the aminonaphthol-sulfonic acid is always introduced into the reaction as aqueous solution, prepared with the use of alkali (see German Offenlegungsschrift No. 2,747,011, (Example 1)).

The known processes have the disadvantage that the aqueous solutions of aminonaphthol sulfonic acids are not sufficiently stable in the neutral or alkaline medium, since, while standing in air, there obviously occur oxidation reactions which, during the subsequent dyestuff production, lead to formation of accompanying colored substances which may qualitatively reduce the shade and fastness of the dyeings. Moreover, in the acylation reaction with the use of such alkaline or neutral aminonaphthol sulfonic acid solutions, there occur secondary reactions if acylation is carried out at a pH above 5.

The present invention provides an improved process for the preparation of dihalogenotriazinylamino-naphthol compounds of the formula (1)

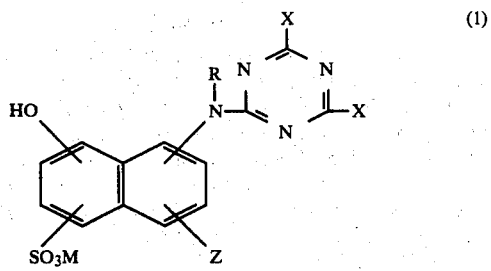

in which the radicals X each mean a fluorine, chlorine or bromine atom, R is a hydrogen atom or an alkyl group of 1-4 C-atoms, such as a methyl or ethyl group, M is a hydrogen atom or the equivalent of a metal, preferably an alkali metal, such as sodium or potassium, and Z is a hydrogen atom or a group of the formula —SO$_3$M with M having the abovementioned meaning which comprises reacting, in water as reaction medium, an aminonaphthol sulfonic acid of the formula (2)

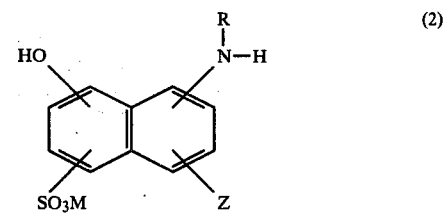

in which R, M and Z have the abovementioned meanings, with M in this case preferably being hydrogen, with a cyanuric halide compound of the formula (3)

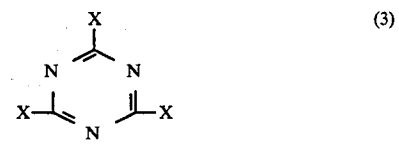

wherein X has the abovementioned meaning, at a pH of 5 or smaller than 5, preferably smaller than 5, the improvement consisting in introducing the aminonaphthol sulfonic acid compound of the formula (2) in solid, undissolved form into the reaction and carrying out the reaction in suspension.

The reaction is preferably carried out at a pH between 1 and smaller than 5, especially at a pH between 1 and 3 with the use of cyanuric chloride or cyanuric bromide and particularly at a pH between 3 and below 5 with the use of cyanuric fluoride as reactant.

The aminonaphthol sulfonic acid compounds of the formula (2) can be introduced into the reaction as dry substance, in crystalline or preferably ground, pulverulent form or in the form of an aqueous suspension with a pH of 5 or smaller than 5. Although the reactants are present in the form of suspensions, acylation occurs rather soon so that it is finished in a relatively short time. In the reaction according to the invention no addition of a customarily usual solvent, for example acetone, for dissolving the cyanuric halide, or solubilizers such as emulsifiers, tensides or similar auxiliaries, are necessary.

Compounds of the formula (2) are, for example, 1-amino-8-naphthol-3,6-disulfonic acid, 1-amino-8-naphthol-4,6-disulfonic acid, 2-amino-5-naphthol-7-sulfonic acid, 2-methylamino-5-naphthol-7-sulfonic acid, 2-amino-8-naphthol-6-sulfonic acid and 2-methylamino-8-naphthol-6-sulfonic acid and their alkali metal salts, such as the mono- and disodium salts.

Compounds of the formula (3) are 2,4,6-trichloro-1,3,5-triazine, 2,4,6-tribromo-1,3,5-triazine and 2,4,6-trifluoro-1,3,5-triazine.

The operation mode according to the invention for the preparation of dihalogenotriazinylamino-naphthol sulfonic acids, which represents to use the aminonaphtholsulfonic acid as reactant in form of the solid substance but not in form of a neutral or alkaline aqueous solution, provides distinct advantages as compared with the known processes; on the one hand, the step of preparing the aminonaphtholsulfonic acid solution may be dispensed with, and on the other, oxidation of the aminonaphtholsulfonic acids in the aqueous solutions, as mentioned above, are avoided. Moreover, the process of the invention substantially suppresses undesired secondary reactions, and purity, quality and yield of the compounds of the formula (1) according to the invention are considerably increased in comparison with the known operation modes. Therefore, it is important for the process according to the present invention to be performed at a pH of 5 or preferably smaller than 5.

The hydrohalic acid liberated during the reaction is preferably bound by an acid-binding agent, without leaving, however, the indicated pH-range of the process. Slightly basic compounds, such as the alkali metal salts of weak acids, such as acetic acid or carbonic acid, for example sodium or potassium carbonate, sodium acetate and sodium bicarbonate, or also disodium hydrogenophosphate, are preferably used. These alkaline, especially weakly alkaline, acid-binding agents may be added to the reaction batch during the reaction in pulverulent form or as aqueous solutions.

The process according to the invention is carried out at a temperature of from −10° C. to +30° C. preferably −5° C. to +20° C. The process is preferably carried out with thorough intermixing, such as vigorous agitation, to ensure a rapid intermixing of the reactants.

The reaction mixtures which are obtained by the process according to the invention and which contain the compounds of the formula (1), can directly be processed as "intermediates" to dyestuffs or their precursors. Thus, these reaction mixtures are used, optionally after previous condensation with a (further) aliphatic or aromatic amine with formation of a secondary condensation product of the triazine, as coupling component for the preparation of azo dyestuffs without previous isolation of the compound of the formula (1).

The following examples illustrate the invention. Parts and percentages are by weight, unless otherwise stated. Parts by weight are related to parts by volume as kilogram to liter.

EXAMPLE 1

319 Parts of 1-amino-8-naphthol-3,6-disulfonic acid as dry, ground material are introduced with stirring into a suspension of 190 parts of finely crystalline cyanuric chloride in 1,300 parts of water and 400 parts of ice. This reaction mixture is stirred for another 3 hours at a temperature of 12° to 16° C. and a pH is maintained at 1.7 to 2.3 by means of about 160 parts of sodium bicarbonate which is added portionwise in pulverulent form. After this time the reaction is complete and no free amine can be detected any more.

A sample of the reaction solution is titrimetrically coupled with any diazonium salt solution, for example with a freshly prepared solution of diazotized aniline, in usual manner. The yield of 1-(4',6'-dichloro-1',3'-5'-triazin-2'-yl)-amino-8-naphthol-3,6-disulfonic acid obtained according to the invention is 95-98% of theory.

The dichlorotriazinylamino-naphthol sulfonic acid prepared in this way can directly be used for the manufacture of an azo dyestuff.

EXAMPLE 2

Within half an hour 319 parts of 1-amino-8-naphthol-4,6-disulfonic acid are added in the form of a dry powder to a suspension of 190 parts of cyanuric chloride in 1,000 parts of water and 700 parts of ice. The temperature is maintained between 0° and +5° C. by addition of ice. The pH is kept at 1.5 to 2.0 by dropwise addition of a saturated aqueous solution of sodium bicarbonate, and thorough stirring of the mixture is continued. After about 3 hours no free amine can be observed any longer.

The yield of 1-(4',6'-dichloro-1',3',5'-triazin-2'-yl)-amino-8-naphthol-4,6-disulfonic acid as determined by means of titration with a diazonium salt is about 98% of theory.

The solution or suspension of the dichlorotriazinylamino-naphthol sulfonic acid as coupling component, obtained in the synthesis, can directly be used for the manufacture of azo dyestuffs.

EXAMPLE 3

239 Parts of 2-amino-5-naphthol-7-sulfonic acid in dry ground form are suspended in 5,000 parts of water. 190 Parts of cyanuric chloride in crystalline form are added while thoroughly stirring and maintaining a temperature of from 5°–10° C. Stirring of this reaction batch is continued for another 3 hours at this temperature while maintaining the pH at 2.5 to 3 by adding pulverulent sodium bicarbonate. After this time no starting compound can be detected any more.

The 2-(4',6'-dichloro-1',3',5'-triazin-2'-yl)-amino-5-naphthol-7-sulfonic acid so prepared is obtained with a yield of more than 95% of theory.

EXAMPLE 4

The process is carried out as described in Example 3 using 253 parts of 2-methylamino-8-naphthol-6-sulfonic acid as aminonathol sulfonic acid. The reaction mixture so obtained which contains the 2-(4',6'-dichloro-1',3',5'-triazin-2'-yl)-methylamino-8-naphthol-6-sulfonic acid with high yield and purity can directly be used for the manufacture of azo dyestuffs.

EXAMPLE 5

The process is carried out as described in Example 1, using 320 parts of cyanuric bromide as acylating agent. The reaction mixture contains the 1-(4',6'-dibromo-1',3',5'-triazin-2'-yl)-amino-8-naphthol-3,6-disulfonic acid with the same yield and purity.

EXAMPLE 6

While stirring thoroughly 135 parts of 2,4,6-trifluoro-1,3,5-triazine are added dropwise at 0° C. to a suspension of 319 parts of ground 1-amino-8-naphthol-3,6-disulfonic acid in 4,000 parts of ice-water. The pH is kept at 3.5 to 4.0 by slowly adding pulverulent sodium bicarbonate. After 30 minutes the reaction is complete. The titrimetrically determined yield of 1-(4',6'-difluoro-1',3',5'-triazin-2'-yl)-amino-8-naphthol-3,6-disulfonic acid is more than 95% of theory.

EXAMPLE 7

140 Parts of 2,4,6-trifluoro-1,3,5-triazine are slowly added to 0° C. with stirring to a suspension of 319 parts of pulverulent 1-amino-8-naphthol-4,6-disulfonic acid in 3,000 parts of ice-water. By slowly adding a saturated aqueous solution of sodium bicarbonate of 0° C., the pH is adjusted at 3.5 to 4.0. Subsequently, stirring of the mixture is continued for 20 to 30 minutes, until not starting compound can be detected any more.

A yield of more than 95% of theory of 1-(4',6'-difluoro-1',3',5'-triazin-2'-yl)-amino-8-naphthol-4,6-disulfonic acid is ascertained by titrimetric determination by means of a diazonium salt solution.

EXAMPLE 8

239 Parts of 2-amino-5-naphthol-7-sulfonic acid in pulverulent form are suspended in 6,000 parts of ice-water. 140 Parts of 2,4,6-trifluoro-1,3,5-triazine are added dropwise while stirring thoroughly, while the temperature is maintained at 0° C. and the pH is adjusted and kept at 3.5 to 4.0 by gradually adding sodium bicarbonate. At this pH stirring of the reaction batch is continued for 20 to 30 minutes until no starting compound can be detected any more.

This reaction mixture contains the 2-(4',6'-difluoro-1',3',5'-triazin-2'-yl)-amino-5-naphthol-7-sulfonic acid with a yield of 95-98% of theory.

The aqueous solution or suspension of this difluorotriazinyl-aminonaphthol sulfonic acid obtained in the synthesis can directly be used for the manufacture of dyestuffs.

EXAMPLE 9

140 Parts of 2,4,6-trifluoro-1,3,5-triazine are slowly added to a suspension of 254 parts of pulverulent 2-methylamino-8-naphthol-6-sulfonic acid in 6,000 parts of icewater, while maintaining the temperature at 0° C. and the pH at 3.5 to 4.0 by adding pulverulent sodium acetate. The reaction batch is thoroughly stirred for another 30 minutes at 0° C. and a pH of 3.5 to 4.0 until no free amine can be detected any more. The mixture obtained contains the 2-(4',6'-difluoro-1',3',5'-triazin-2'-yl)-methylamino-8-naphthol-6-sulfonic acid with a yield of more than 95% of theory.

EXAMPLE 10

The solution or suspension of dichlorotriazinylaminonaphthol-disulfonic acid prepared as described in Example 1 in accordance with the process of the invention, can be further processed as follows: For carrying out a coupling reaction to give an azo dyestuff, a hydrochloric aqueous diazonium salt solution, prepared in the usual way, from 173 parts of aniline-2-sulfonic acid is added to said solution or suspension. Coupling is performed at a pH of 4.5 to 5.0 which is first maintained by adding 15 parts of sodium dihydrogenophosphate and subsequently by adding sodium bicarbonate. Coupling is carried out at 15° to 18° C. When no diazonium compound is detected any more by a spot test, a solution of 300 parts of 4-β-sulfato-ethylsulfonyl-anilne and 105 parts of sodium bicarbonate in 1,000 parts of water are added to this azo compound formed. Stirring of this reaction mixture is continued at a pH of from 5.5 to 6.0 first for 1 hour at 25°-30° C.; subsequently the reaction temperature is slowly raised to 50° C. within 2 hours. The dyestuff formed is precipitated with potassium chloride, and isolated. The dyestuff of the formula

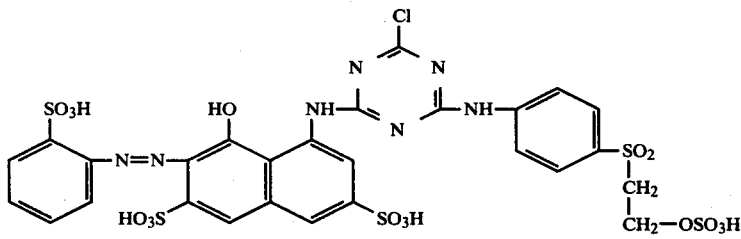

known from German Patent Specification No. 1,265,698 is obtained as potassium/sodium salt. Calculated on the aminonaphthol-disulfonic acid used as starting compound, this dyestuff is obtained with a yield higher by 10% than that obtainable from the process described in the above German Patent Specification. Moreover, this dyestuff obtained from the precursor prepared according to the invention yields dyeings on wool which have considerably improved wet fastness, above all a better fastness to washing at 60° C. and a clear superiority in the alkaline fastness to perspiration.

We claim:

1. In a process for the preparation of a dihalogenotriazinylamino-naphthol compound of formula (1)

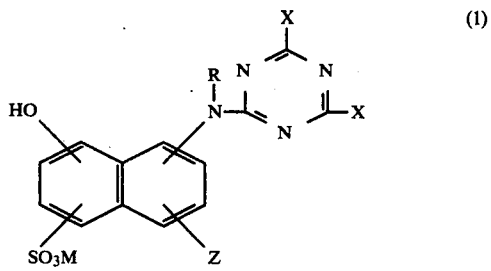

in which each X is fluorine, chlorine or bromine, R is hydrogen or alkyl of 1–4 C-atoms, M is hydrogen or the equivalent of a metal and Z is hydrogen or a group of the formula —SO₃M with M defined above, comprising reacting an aminonaphthol compound of formula (2)

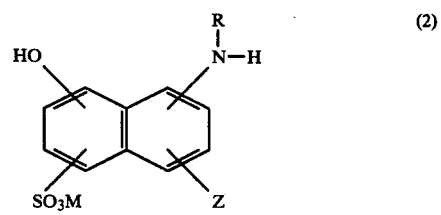

in which R, M and Z are defined as above, with M in formula (2) preferably being hydrogen, with a cyanuric halide compound of the formula (3)

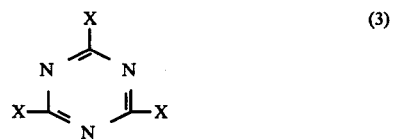

in which X is defined as above, in water as reaction medium at a pH of 5 or smaller than 5, the improvement consisting in introducing the aminonaphthol compound of formula (2) in solid, undissolved form into the reaction and carrying out the reaction in suspension.

2. A process according to claim 1, wherein the reaction is carried out at a pH between 1 and below 5.

3. A process according to claim 1, wherein the reaction is carried out with 2,4,6-trichloro-1,3,5-triazine at a pH between 1 and 3.

4. A process according to claim 1, wherein the reaction is carried out with 2,4,6-trifluoro-1,3,5-triazine at a pH from 3 to below 5.